United States Patent [19]

Pilacinski et al.

[11] Patent Number: 5,301,540

[45] Date of Patent: Apr. 12, 1994

[54] PROBE FOR MEASURING THE VISCOSITY OF LIQUIDS

[76] Inventors: Wlodzimierz Pilacinski, ul. Wokalna 4 Apt. 13, 02-783 Warsaw; Boguslaw Korecki, Al. Rew. Pazdziern. 151 Apt. 61, 01-424 Warsaw; Leon Gradon, ul. Dunikowskiego 12 Apt. 17, 02-784 Warsaw; Ryszard Plowiec, ul. Sobieskiego 70a Apt. 56, 02-430 Warsaw; Andrzej Kaczynski, ul. Zakroczymska 7 Apt. 7, 00-225 Warsaw; Jacek Bodasinski, ul. J.S. Bacha 26b Apt. 108, 02-764 Warsaw; Ryszard Kurzawa, ul. Sloneczna 21 Apt. 7, 34-410 Rabka, all of Poland

[21] Appl. No.: 61,738

[22] Filed: May 17, 1993

[51] Int. Cl.⁵ .................... G01N 11/06; G01N 11/16
[52] U.S. Cl. .................... 73/54.24; 73/54.25; 73/54.26; 73/54.41
[58] Field of Search ........... 73/54.41, 59, 60, 54.24, 73/54.25, 54.26

[56] References Cited

U.S. PATENT DOCUMENTS

| | | | |
|---|---|---|---|
| 3,796,088 | 3/1974 | Gustafsson et al. | 73/59 |
| 4,799,378 | 1/1989 | Portman, Jr. et al. | 73/54 |
| 4,862,384 | 8/1989 | Bujard | 364/509 |
| 4,893,496 | 1/1990 | Bau et al. | 73/32 A |
| 4,920,787 | 5/1990 | Dual et al. | 73/54 |
| 4,926,682 | 5/1990 | Holm-Kennedy et al. | 73/54 |

OTHER PUBLICATIONS

W. H. Robinson et al, "Piezoelectric Method of Determining Viscosity at 40 KHz", Journal of Applied Physics, Band 49, No. 3, Mar. 1978.

*Primary Examiner*—James C. Housel
*Assistant Examiner*—N. Bhat
*Attorney, Agent, or Firm*—Michael I. Kroll

[57] ABSTRACT

A probe for measuring the viscosity of small quantities of liquids is described. The probe for measuring the viscosity of liquids, including a housing having a surface, a first end point, and a second end point, the housing having a first, a second, and a third segment, an electric cable clamp being fixed at the first end, a transducer with electrodes on the surface of the housing, a rod containing a surface to which is glued the electrodes, the rod having a length with a free end, nodal points are attached to the first, second, and third segments of the housing, and, a clamp attaches the rod to the nodal points.

6 Claims, 1 Drawing Sheet

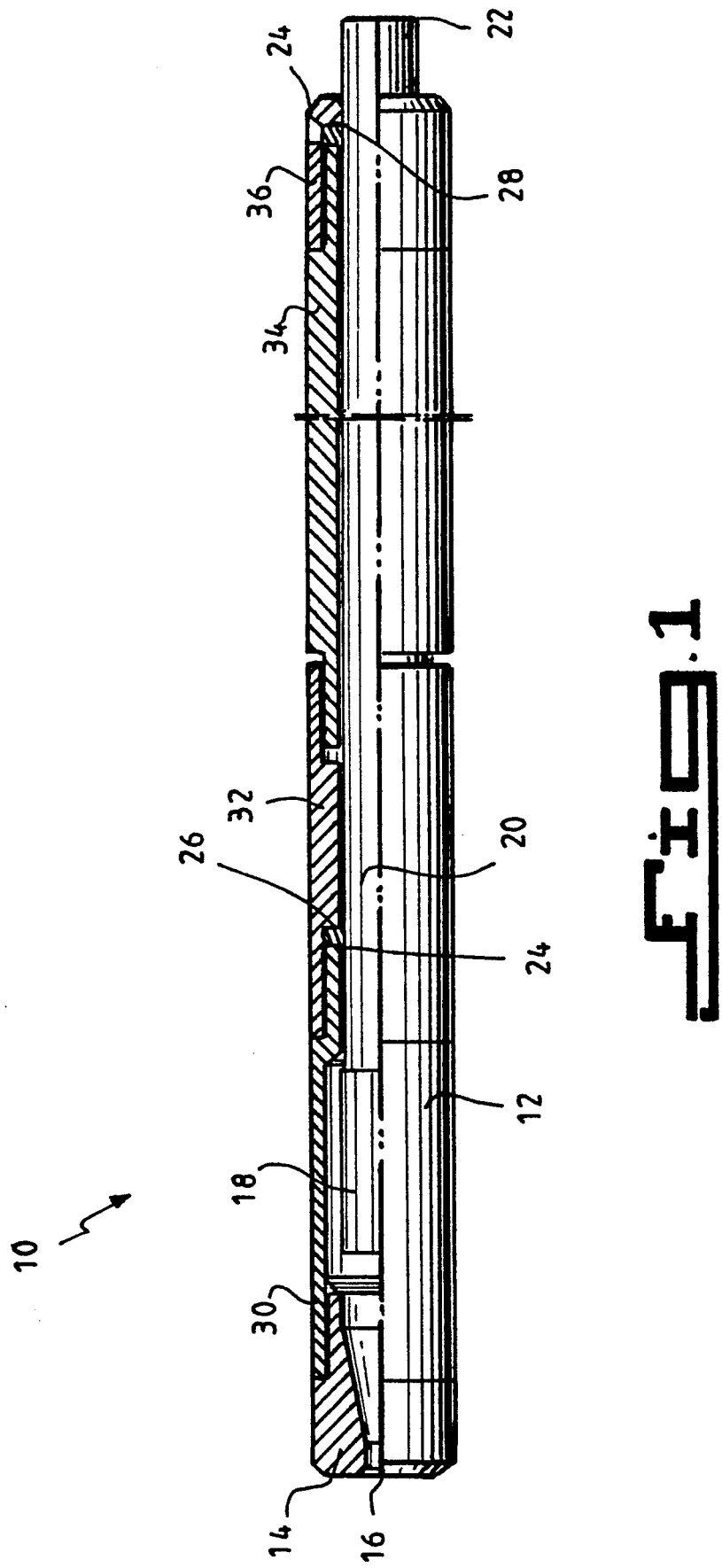

PROBE FOR MEASURING THE VISCOSITY OF LIQUIDS

BACKGROUND OF THE INVENTION

1. Field of the Invention

The present invention relates to a probe for the measurement of the viscosity of liquids.

More particularly, the present invention relates to a probe for measuring the viscosity of biological liquids.

2. Description of the Prior Art

A probe, known in the prior art, measures the viscosity of liquids. It uses a magnetostriction transducer. The magnetic field of the coil contains a ferrite core. The rod face is made of an elastic material to which is glued the transducer face. The elastic material is fusible quartz. The other end of the rod is used as the sensor for the measurement of viscosity.

The common housing contains the transducer and the rod. At one of the nodal points of the rod a clamp is disposed for clamping the rod. An externally stimulated generator operates the coil. The operation of the generator creates the generation of a magnetic field. The ferrite core is caused to vibrate by the magnetic coil. The sensor is in the test liquid where it receives the vibrations from the quartz rod.

The measurement of the viscosity of a liquid consists in measuring the vibration damming introduced by the liquid under test and comparing the reading to the value of the damping under conditions of free vibration. By mounting the clamp of the ferrite rod at a nodal point, the damping introduced by the clamp can be reduced.

However, a drawback of such a probe is a low output signal from the magnetostriction transducer. The core can be displaced with respect to the coil due to the clamping of the rod at one point only, and, in consequence, the measurement accuracy is worsened.

Owing to the poor coupling between the ferrite core and the coil, it is impossible to build a generator operating at the natural frequency of the transducer because the transducer feedback is too weak.

Numerous innovations for probes for measuring he viscosity of biological liquids have been provided in the prior art that are adapted to be used. Even though these innovations may be suitable for the specific individual purposes to which they address, they would not be suitable for the purposes of the present invention as heretofore described.

SUMMARY OF THE INVENTION

Accordingly, it is an object of the present invention to provide a probe for measuring the viscosity of small quantities of liquids, including biological liquids that avoids the disadvantages of the prior art.

The use of a piezoelectric transducer of high efficiency permits the clamps at two nodal points to be employed and this prevents the rod displacement while allowing for repeatable readings.

The probe of the present invention, owing to the use of a piezoceramic transducer, permits the transducer to be excited to vibrate at a resonant frequency. This enables the sensitivity to be improved and permits the physical disturbance effects to be removed.

Furthermore, the clamps are fitted with a facility for adjusting the clamping force.

The probe of the present invention is characteristic that the transducer is a piezoceramic transducer with electrodes attached directly to its surface while the rod is mounted in clamps located at two extreme nodal points to the advantage of the transducer. The housing consists of segments fitted with axial adjustment controls for the rod mounting points.

In keeping with these objects, and with others which will become apparent hereinafter, one feature of the present invention resides, briefly stated, in a probe for measuring the viscosity of biological liquids, including a housing having a surface, a first end point, and a second end point, the housing having a first, a second, and a third segment, a transducer with electrodes on the surface of the housing, a rod containing a surface to which is glued the electrodes, the rod having a length with a free end, nodal points are attached to the first, second, and third segments of the housing, and, a clamp attaches the rod to the nodal points.

In accordance with another feature of the present invention, the transducer is cylindrical and made of piezoelectric ceramic.

Another feature of the present invention is that the extending rod is fusible-quartz.

Yet another feature of the present invention is that the free end of the rod is the sensor portion for the measurement of the viscosity of liquids.

Still another feature of the present invention is that the housing is terminated by an elbow.

Yet still another feature of the present invention is that the length of the rod is selected so that the end of the rod will vibrate and serve as the sensor.

The novel features which ar considered characteristic for the invention are set forth in particular in the appended claims. The invention itself, however, both as to its construction and its method of operation, together with additional objects and advantages thereof, will be best understood from the following description of the specific embodiments when read in connection with the accompanying drawing.

BRIEF DESCRIPTION OF THE DRAWING

FIG. 1 is a cross-sectional drawing of the probe for measuring the viscosity of biological liquids of the present invention, with parts left covered.

LIST OF REFERENCE NUMERALS UTILIZED IN THE DRAWING

10—probe of the present invention
12—housing of the probe 10
14—electric cable clamp
16—one end
18—cylindrical ceramic transducer
20—rod
22—free end of the rod 20
24—clamps
26—nodal point
28—nodal point
30—segment of the housing 12
32—segment of the housing 12
34—segment of the housing 12
36—elbow

DETAILED DESCRIPTION OF THE PREFERRED EMBODIMENT

The probe 10 includes a housing 12 with an electric cable clamp 14 fixed at its one end 16. A cylindrical ceramic transducer 18 with electrodes on the surface of the housing 12, is glued to the fusible-quartz rod. The free end 22 of the rod 20 is a sensor for the measurement of the viscosity of liquids. Clamps 24 attach the rod 20 at two nodal points 26 and 28. The nodal points 26 and 28 are attached to the segments 30, 32, 34 of the housing 12, which is terminated by an elbow 36, that along with the segments 30, 32, 34 contain threads for axial adjustment.

The probe 10 operates, as described below. The electric output from a generator (not shown in this figure) is connected to the electrodes of the piezoceramic transducer 18. Owing to the applied voltage, the transducer 18 torsionally vibrates. Its vibrations are transferred via the face surface, of the bound cylindrical rod 20. The bound cylindrical rod 20 is made of fusible quartz. The length of the rod 20 is selected so that the vibration antinode is located at the rod end which provides the sensor 22.

With the probe 10 immersed in the liquid under test and the vibration under a steady-state condition, the generator output is momentarily disconnected and, in consequence, the rod 20 performs free vibration that is damped due to the viscosity of the liquid. The increasing vibrations of the rod 20 are transferred to the transducer 18 which operates as a piezoelectric transducer and generates a signal which is proportional to the vibration amplitude of the quartz rod 20 while the vibration decay rate is a measure of the viscosity.

It will be understood that each of the elements described above, or two or more together, may also find a useful application in other types of constructions differing from the type described above.

While the invention has been illustrated and described as embodied in a probe for measuring the viscosity of biological liquids, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A probe for measuring the viscosity of liquids, comprising:
   a) a housing having a surface, a first end point, and a second end point, said housing having a first, a ,second, and a third segment each being operably connected in sequence;
   b) an electric cable clamp being fixed at said first end;
   c) a transducer comprising electrodes on said surface of said transducer, transducer being disposed within said housing;
   d) a quartz rod having a length with a first end connected to said transducer and extending from said third housing segment a free end which senses the viscosity of liquids;
   e) transducer nodal points along said first, second, and third segments of said housing; and,
   f) a clamp attaching said rod at each nodal point.

2. A probe as defined in claim 1, wherein said transducer is cylindrical and made of piezoelectric ceramic.

3. A probe as defined in claim 2, wherein said rod is fusible-quartz.

4. A probe as defined in claim 3, wherein said free end of said rod is a sensor portion for the measurement of the viscosity of liquids.

5. A probe as defined in claim 4, wherein said housing is terminated by an elbow.

6. A probe as defined in claim 5, wherein said length of said rod is selected so that said end of said rod will vibrate and provide said sensor.

* * * * *